US00PP28030P3

(12) United States Plant Patent
van Kleinwee

(10) Patent No.: US PP28,030 P3
(45) Date of Patent: May 16, 2017

(54) *PETUNIA* PLANT NAMED 'PEHY0015'

(50) Latin Name: *Petunia hybrida*
Varietal Denomination: PEHY0015

(71) Applicant: SYNGENTA PARTICIPATIONS AG, Basel (CH)

(72) Inventor: Theodorus Cornelis van Kleinwee, Enkhuizen (NL)

(73) Assignee: Syngenta Particpations AG, Basel (CH)

( * ) Notice: Subject to any disclaimer, the term of this patent is extended or adjusted under 35 U.S.C. 154(b) by 0 days.

(21) Appl. No.: 14/998,447

(22) Filed: Jan. 5, 2016

(65) Prior Publication Data

US 2016/0198613 P1 Jul. 7, 2016

Related U.S. Application Data

(60) Provisional application No. 62/099,638, filed on Jan. 5, 2015.

(51) Int. Cl.
*A01H 5/02* (2006.01)

(52) U.S. Cl.
USPC ..... Plt./356.22

(58) Field of Classification Search
USPC ..... Plt./356.22
CPC ..... A01H 5/02
See application file for complete search history.

*Primary Examiner* — Kent L Bell
(74) *Attorney, Agent, or Firm* — Dale Skalla

(57) ABSTRACT

A new *Petunia* plant named 'PEHY0015' particularly distinguished by the purple flowers, relatively early flowering, medium green foliage, good branching, a semi-trailing habit, and large flowers.

1 Drawing Sheet

Latin name of the genus and species of the plant claimed: *Petunia hybrida.*

Varietal denomination: 'PEHY0015'.

BACKGROUND OF THE NEW PLANT

The present invention comprises a new *Petunia*, botanically known as *Petunia hybrida*, and hereinafter referred to by the variety name 'PEHY0015'.

'PEHY0015' is a product of a planned breeding program. The new cultivar has purple flowers, relatively early flowering, medium green foliage, good branching, a semi-trailing habit, and large flowers.

'PEHY0015' originated from a hybridization made in October 2010 in a controlled breeding environment in Enkhuizen, Netherlands. The female parent was the unpatented proprietary plant designated 'N0116-1' with purple-rose flower color and a very flat and vigorous plant habit.

The male parent of 'PEHY0015' was an unpatented proprietary plant identified as 'N0177-1' with deep rose flower color, a mounding plant habit, and having relatively low vigor.

The resulting seeds were sown in February 2011. 'PEHY0015' was selected as a single flowering plant within the progeny of the stated cross May 25, 2011 in a controlled environment in Enkhuizen, Netherlands.

The first act of asexual reproduction of 'PEHY0015' was accomplished when vegetative cuttings were propagated from the initial selection in June 2011 in a controlled environment in Enkhuizen, Netherlands.

BRIEF SUMMARY OF INVENTION

Horticultural examination of plants grown from cuttings of the plant initiated in September 2011 in Angers, France, and continuing thereafter, has demonstrated that the combination of characteristics as herein disclosed for 'PEHY0015' are firmly fixed and are retained through successive generations of asexual reproduction.

'PEHY0015' has not been observed under all possible environmental conditions. The phenotype may vary significantly with variations in environment such as temperature, light intensity, and day length.

A Plant Breeder's Right for this cultivar was applied for in the European Community Plant Variety Office (CPVO) on Jul. 14, 2014, No. 2014/1723. 'PEHY0015' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0015' with colors being as true as possible with an illustration of this type.

Figure 1:
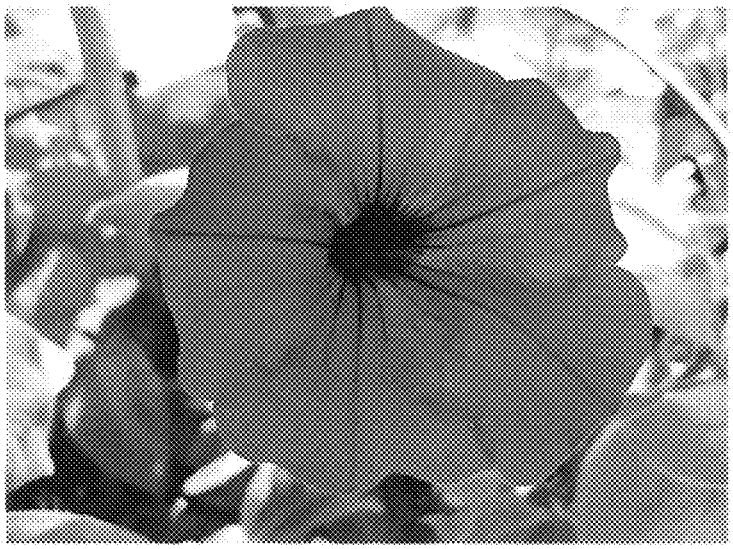
Figure 2:
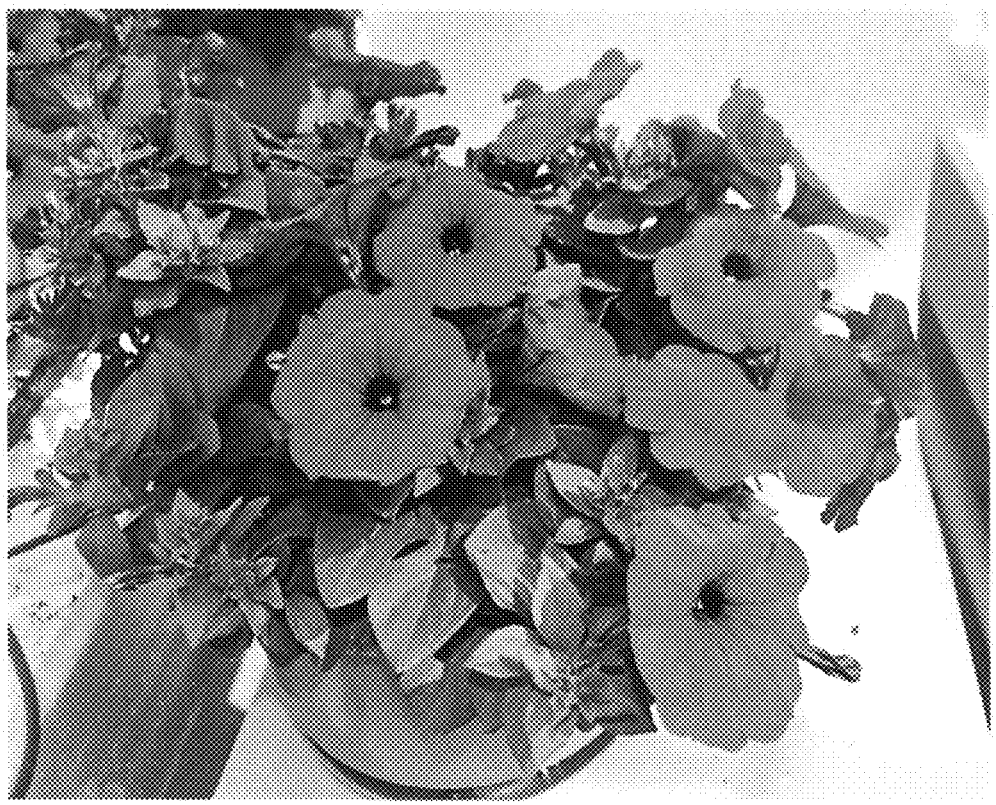

The photographic drawing shows in FIG. 2. a flowering plant of the new variety and in FIG. 1. a close-up of a flowers.

DETAILED BOTANICAL DESCRIPTION

The plant descriptions and measurements were taken around Oct. 1, 2014, from plants grown for breeding purposes in a greenhouse in Enkhuizen, Netherlands. The plants had been planted around Jul. 10, 2014. They were approximately 12 weeks of age and growing in 19 cm containers. They had been cut back a few weeks before the observations.

The aforementioned photographs were taken in April 2014 from plants growing in a greenhouse trial in Andijk, Netherlands. These plants were approximately 12-13 weeks of age.

Color references are made to The Royal Horticultural Society Colour Chart (R.H.S.) 2001.

TABLE 1

DIFFERENCES BETWEEN THE NEW VARIETY 'PEHY0015' AND A SIMILAR VARIETY

| | 'PEHY0015' | 'PEHY0003', also known as 'Sanguna Purple Improved', U.S. Plant Pat. No. 23,644 |
|---|---|---|
| Leaf, shape: | More elliptic | Ovate |
| Plant habit: | Compact, semi-upright to creeping | More upright, less compact |
| Branching: | Very good branching | Less branching |

Plant:

*Form, growth and habit.*—Good branching, semi-trailing habit.

*Plant height.*—8 cm.

*Plant height (inflorescence included).*—12 cm.

*Plant width.*—30 cm.

Roots:

*Number of days to initiate roots.*—About 12 days at about 22 degrees C.

*Number of days to produce a rooted cutting plant.*—18-24 days at about 22 degrees C.

*Type.*—Fine, fibrous, free branching.

*Color.*—RHS N155B.

Foliage:

*Arrangement of leaves.*—Simple, opposite, sometimes decussate.

*Immature leaf, color upper surface.*—RHS 138A.

*Immature leaf, color lower surface.*—RHS 144A.

*Mature leaf, color upper surface.*—RHS 137B.

*Mature leaf, color lower surface.*—RHS 146B.

*Length.*—7.5-9 cm.

*Width.*—3.5-4.2 cm.

*Shape.*—Ovate.

*Base shape.*—Obtuse.

*Apex shape.*—Obtuse.

*Margin.*—Entire, somewhat wavy.

*Texture, upper surface.*—Hirsute.

*Texture, lower surface.*—Hirsute.

*Color of veins, upper surface.*—RHS 144A.

*Color of veins, lower surface.*—RHS 144A.

*Petiole color.*—RHS 144B.

*Length.*—0.5-0.6 cm.

*Diameter.*—0.4 cm.

*Texture.*—Hirsute, with longer hair on the edges.

Stem:

*Quantity of main branches per plant.*—4-6.

*Color of stem.*—RHS 144A.

*Length of stem.*—8-10 cm.

*Diameter.*—0.5 cm.

*Length of internodes.*—3-3.5 cm.

*Texture.*—Hirsute, glandular hair.

*Color of pedicels.*—RHS 144A to RHS 144B, darker at base of flower, RHS N77A.

*Length.*—2.5-3 cm.

*Diameter.*—0.2 cm.

*Texture.*—Hirsute.

Inflorescence:

*Type of inflorescence.*—Single flowers, emerging from the upper nodes of the stem.

*Blooming habit.*—Continuous flowering throughout the summer months, little affected by heat.

*Start of flowering.*—About 8 weeks from planting rooted cuttings.

*Quantity of flowers per plant.*—About 15.

*Lastingness of individual blooms on the plant.*—Up to 14 days, depending on temperature.

*Fragrance.*—None.

Bud (just when opening/showing color):

*Color.*—From the base to the top: RHS 83A to RHS N92A a little green part, RHS 144B near the top.

*Length.*—4.5 cm.

*Width.*—1.8 cm at the top.

*Shape.*—Oblong.

Immature flower:

*Diameter.*—5 cm.

*Color, upper surface.*—Very deep RHS N74A.

*Color, lower surface.*—RHS N78A.

Mature flower:

*Shape.*—Salver-shape, with funnel shape base, formed by 5 fused petals.

*Flower, horizontal diameter.*—6.5 cm.

*Flower, vertical diameter.*—5.3 cm.

*Shape.*—Salver-shape, with funnel shape base, formed by 5 fused petals.

*Corolla, color upper surface.*—Deep RHS N74A, with only very weak dark veins, color near RHS 187A, but very fine.

*Corolla, color lower surface.*—RHS N78A to RHS N78B.

*Apex shape.*—Mucronalate.

*Petal base shape.*—Fused.

*Petal margin.*—Entire.

*Waviness of petals margin.*—Weak to medium.

*Petal lobation.*—Weak to medium.

*Petal texture, upper surface.*—Glabrous, papillose.

*Petal, texture, lower surface.*—Papillose, short hair to tube, then hirsute with longer hair.

*Corolla tube color inside.*—Appears black, as the pattern of veins is very dense, color RHS N186A, and RHS 77A for the background color.

*Corolla tube, color outer surface.*—RHS 79B.

*Corolla tube length.*—3.5-4 cm.

*Corolla texture.*—Glabrous inside, hirsute outside.

Calyx:

*Form.*—5 sepals in a whorl, fused at the base.

*Color of sepal, upper surface.*—RHS 137B.

*Color of sepal, lower surface.*—RHS 137D.

*Length.*—2.7-3 cm.

*Width.*—0.5-0.7 cm.

*Shape.*—Ensiform, fused at the base.

*Apex shape.*—Acute.

*Base.*—Fused.

*Margins.*—Entire.

*Texture, upper surface.*—Hirsute.

*Texture, lower surface.*—Hirsute with shorter hair than upper surface.

Reproductive organs:

*Gynoecium.*—Pistil: 1. Length: 2.5 cm. Style color: RHS 145B, green at the base, to RHS 79C near the stigma. Style length: 2.3 cm. Stigma color: Green, RHS 145A, for the upper side, and RHS 79C for the lower side. Stigma shape: Flat rounded disc fixed on the style from under. Ovary color: RHS 143C.

*Androecium*.—Stamens: Color of filaments: RHS 157C, tone of RHS 77B near the anthers. Length filaments: 2.4 cm. Anther color: Same as pollen. Anther length: 0.1 cm. Anther shape: Elliptical. Color of pollen: Grey-bluish color, near RHS 122A. Pollen amount: Plenty.

Fertility/seed set: Has not been observed on this hybrid.

Disease/pest resistance: Has not been observed on this hybrid.

What is claimed is:

1. A new and distinct variety of *Petunia* plant named 'PEHY0015' substantially as illustrated and described herein.

* * * * *